Sept. 24, 1974 R. S. MOORE Plant Pat. 3,627
MINIATURE ROSE PLANT
Filed Sept. 24, 1973
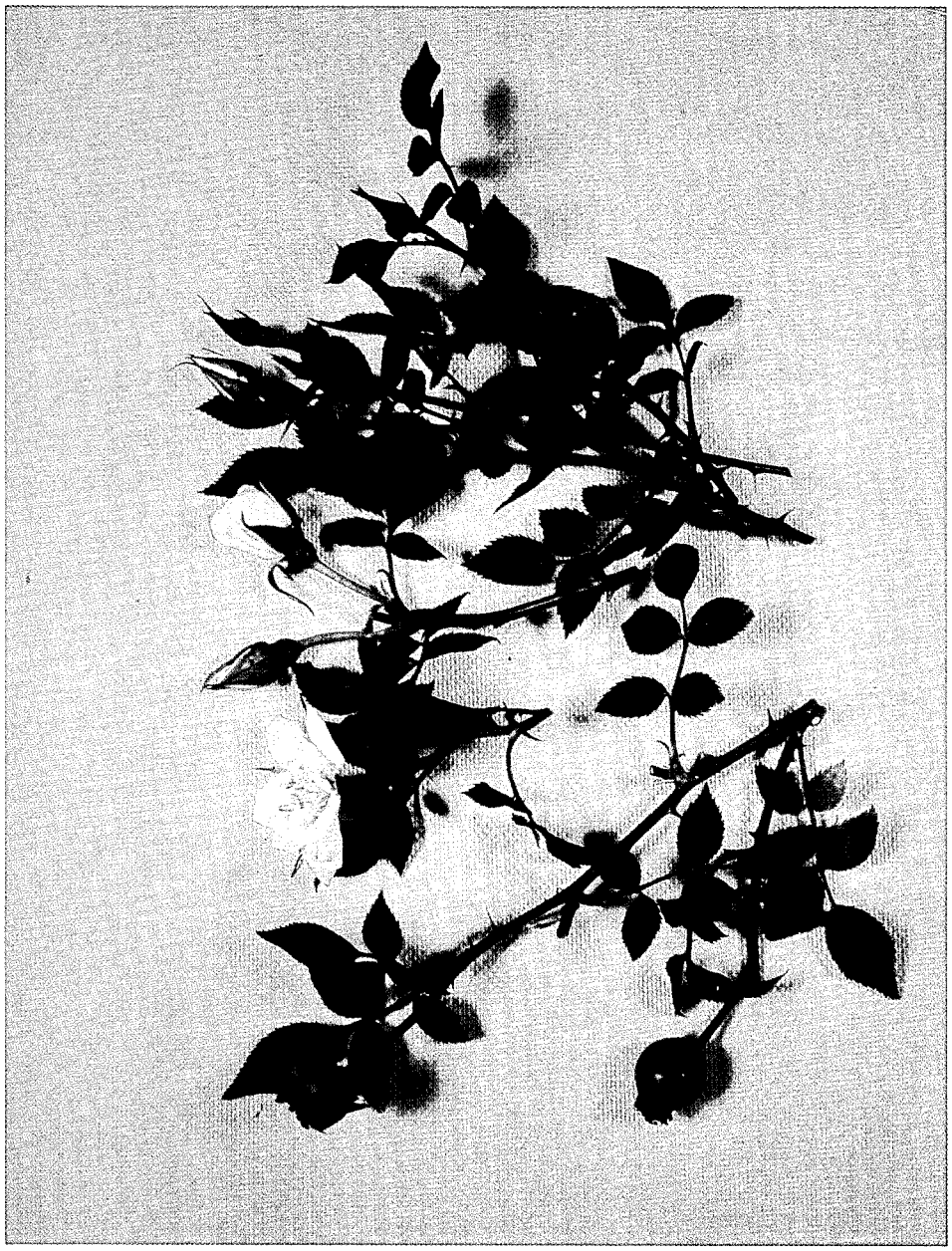

United States Patent Office

Plant Pat. 3,627
Patented Sept. 24, 1974

3,627
MINIATURE ROSE PLANT

Ralph S. Moore, 2519 E. Noble Ave.,
Visalia, Calif. 93277

Filed Sept. 24, 1973, Ser. No. 400,420
Int. Cl. A01h 5/00
U.S. Cl. Plt.—8 1 Claim The present invention relates to a new and distinct variety of hardy, dwarf, bush type rose plant of the miniature class; the variety being primarily characterized—as to novelty—by semi-double yellow flowers which, as compared to Yellow Doll (Pat. 2,450), are similar in bud form but of a deeper yellow color and fully open flowers are less double.

The variety is further characterized by:

An abundance of bloom, with flowers on mature plants borne singly and in clusters of three to five to the stem.

A plant which is vigorous, of rounded compact habit and tending to grow more spreading than tall, with semi-glossy, dark green leaves;

A plant, which has a normal average height of about 12"–14" at maturity, resembling the general plant habit of Yellow Doll (Pat. 2,450) miniature rose;

A plant which grows and blooms satisfactorily in the greenhouse, outdoors in pots or in the garden; and provides attractive cut flowers.

The present variety of miniature rose was originated by me in my nursery located at Visalia, Calif., under conditions of careful control and observation, as a cross of Golden Glow (Pat. 263—expired) as the seed parent X an unnamed near-white seedling (miniature) as the pollen parent.

Subsequently to origination of the variety I successfully asexually reproduced it, in my nursery located as aforesaid, by budding as well as by cuttings; the reproductions having run true in all respects.

The color photograph illustrates a spray, including foliage, buds and flowers.

Referring now specifically to the new and distinct variety of miniature rose plant, the following is a detailed description thereof in outline; all major color identifications being by reference to the British Colour Council Horticultural Colour Chart, except where common terms of color definition are employed.

Type: Hardy; dwarf; bush; seedling; outdoors; greenhouse, garden decoration; cut flowers.

Class: Miniature.

Flowers: Continuity—continuous repeat bloom during normal growing season. May be flowered out of season in greenhouse.

*Fragrance*—Slight to moderate.

Flowers borne: Singly on young plants; and singly or several together in cluster, on medium length sturdy stem, on mature plants.

Quantity of blooms: Average abundance.

Bud: Peduncle—medium length; sturdy; erect; medium to dark green.

Before calyx breaks — size — small. Form; long pointed, usually with very few short appendages on surface of the bud; with foliaceous parts extending beyond the tip of the bud equal to one-half or less of its length.

*Color:* Medium green.

*As calyx breaks:* Color—deep yellow (sometimes almost orange). As first petal opens: size—small.

*Form:* Long pointed. Color—outside: Chinese Yellow 606, sometimes with a slight greenish tinting near base and often (outdoors) tinted or splashed with red on side of bud exposed to direct sun; inside: Chinese Yellow 606, sometimes with a slight greenish cast.

*Opening:* Usually opens well in all weather.

Bloom: Size when fully open—small—about 1¼"–1⅜".

*Petalage:* Semi-double, varies with the season but averages about 10 petals.

*Form:* Open—with stamens and pistils showing—petals arranged in loose informal pattern.

Petals: Satiny on upper surface; satiny on lower surface.

*Shape:* Outside petals broad lanceolate (almost round) with short acute tip; intermediate—broad lanceolate with short acute tip; inside—lanceolate but not always of regular shape.

*Color: Newly opened flower from plant grown outdoors (September 1973), Visalia, Calif.:* Outside petal: Outside surface—Chinese Yellow 606 to 606/1—sometimes splashed with red (outdoors). inside surface—Chinese Yellow 606; Intermediate petal: Outside surface—Chinese Yellow 606 to 606/1; inside surface—Chinese Yellow 606. Inner petal: Outside surface—same as intermediate petal; inside surface—same as intermediate petal.

General color effect: Newly opened flower—deep yellow. Three days open—lighter yellow.

Behaviour: Drop off clean.

Flower longevity (September 1973), bush in garden 3–4 days or longer. Cut flowers kept at living room temperature—3 days.

Reproductive organs:

*Stamens:* Normal.

*Anthers:* Normal.

*Pollen:* Abundant.

*Pistils:* Modernate number.

*Styles:* Fairly even, medium length, bunched.

*Stigma:* Usually well formed and functional.

*Ovaries:* All enclosed in calyx.

*Hips:* Few, round, greenish to orange, few seeds.

Foliage:

*Leaves:* Compound of 5 (sometimes 3) leaflets; abundant, medium small, leathery, semi-glossy.

*Leaflets:* Shape; lanceolate; apex acute, base less acute.

*Margin:* Serrate. Color: medium to dark green; new leaves sometimes lightly tinted reddish or bronze—serrated.

*Rachis:* Strong; upper surface grooved with a few or no short hairs or prickles; under side sparsely thorny.

*Stipules:* Medium to long; narrow width; relatively short points, turning out at an angle of 45 degrees or more.

Growth:

*Habit:* Compact; bushy; moderately spreading; much branched.

*Growth:* Vigorous.

*Canes:* Medium to strong, stocky.

*Main stems:* Color: medium to dark green.

*Thorns:* Moderately thorny; long oval base; medium length; slender; hooked slightly downward. Color—brown.

*Prickles:* None.

*Hairs:* None.

Branches—Color: medium green. Thorns: moderately thorny; medium length; slender; hooked slightly downward; long oval base; color—brown.

New Shoots—color: medium to bright green, sometimes lightly tinted reddish; thorns; moderately thorny; medium to long, slender; hooked slightly downward; long oval base.

*Color:* Reddish to brown.

*Prickles:* None.
*Hairs:* None.

The miniature rose plant and its flowers as herein described may vary slightly in detail due to climatic, soil and cultural conditions under which the variety may be grown; the present description being of the variety as grown at Visalia, Calif.

The following is claim:

1. A new and distinct variety of miniature rose plant of hardy, dwarf, rounded, much branched, bush type, as illustrated and described, characterized by slender, very yellow buds (sometimes tinted or splashed lightly with red when grown outdoors) with long green sepals which tend to remain against the buds as they open, instead of reflexing downward as is common with most hybrid tea roses, and flowers resembling the Yellow Doll (Pat. 2,450) miniature rose in color and general effect but less double, the petals of which are generally more broad and the color being a darker yellow; the bush being more spreading when young; and further characterized by a plant which is vigorous in growth, yet compact, easy to propagate from cuttings, with small to medium size, medium to dark green foliage, an abundance of bloom, with flowers borne singly and several to the stem (on mature plants) in well arranged clusters.

No references cited.

ROBERT E. BAGWILL, Primary Examiner